United States Patent
Eliaz

(10) Patent No.: US 6,462,029 B1
(45) Date of Patent: Oct. 8, 2002

(54) COMPOSITIONS AND METHODS FOR TREATING MAMMALS WITH MODIFIED ALGINATES AND MODIFIED PECTINS

(75) Inventor: Isaac Eliaz, Sebastopol, CA (US)

(73) Assignee: Econugenics, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/883,329

(22) Filed: Jun. 19, 2001

Related U.S. Application Data

(63) Continuation-in-part of application No. 09/255,265, filed on Feb. 23, 1999, now Pat. No. 6,274,566.

(51) Int. Cl.$^7$ ................... A61K 31/732; A61K 31/734
(52) U.S. Cl. ........................................................ 514/54
(58) Field of Search ........................................... 514/54

(56) References Cited

U.S. PATENT DOCUMENTS

| | | | |
|---|---|---|---|
| 5,141,927 A | 8/1992 | Krotkiewski | 514/54 |
| 5,283,076 A | 2/1994 | Kazuyuki et al. | 426/575 |
| 5,324,526 A | 6/1994 | Iwata | 426/2 |
| 5,597,810 A | 1/1997 | Hoffman et al. | 514/54 |

FOREIGN PATENT DOCUMENTS

| | | | |
|---|---|---|---|
| JP | 61064701 | * | 9/1993 |
| JP | 09235234 | | 9/1997 |

OTHER PUBLICATIONS

Pienta et al. Journal of the National Cancer Institute, 87/5, pp. 348–352 (Mar. 1, 1995).*

Kimura, et al., "Pharmaceutical Evolution of Ibuprofen Fast–Absorbed Syrup Containing Low Molecular–weight Gelatin", J. Pharm. Sci., vol. 81, No. 2, pp. 141–144, Feb. 1992 (Abstract).

Kimura, et al., J. Enthnopharmacol, vol. 54, No. 1, pp. 47–54, 1996 (Abstract).

N.G. Schipper, et al., "Chitosans as Absorption Enhancers for Poorly Absorbable Drugs. 1: Influence of Molecular Weight and Degree of Acetylation on Drug Transport Across Human Intestinal Epithelial (Caco–2) Cells", Pharm. Res., vol. 13, No. 11, pp. 1686–1692, Nov. 1996 (Abstract).

L.R. Schiller, et al., "Validation of Polyethylene Glycol 3350 as a Poorly Absorable Marker for Intestinal Perfusion Studies", Dig. Dis. Sci., vol. 42, No. 1, pp. 1–5, Jan. 1997 (Abstract).

T. Lindmark, et al., "Absorption Enhancement in Intestinal Epithelial Caco=2 Monolayers by Sodium Captrate: Assessement of Molecular Weight Dependence and Demonstration of Transport Routes", vol. 5, No. 3, pp. 215–223, 1998 (Abstract) J. Drag Target.

Sumita Jain, et al., "Deletion of algK in Mucoid Pseudomonas Aeruginosa Blocks Alignate Polymer Formation and Results in Uronic Acid Secretion", J. Bac., pp. 634–641, Feb. 1998 (Abstract).

Murata Kousaku, et al., "Microbial enzymes and their application to pharmaceutical areas", Department of Food Safety and Utilization, vol. 19, pp. 32–46, Nov. 24, 1998.

Fredrik Hed, et al., "Adsorption of charged drugs to oppositely charged polysaccharides—a study of the influence of polysaccharide structure and hydrophobicity of the drug molecules", on–line at http://www.geocities.com/hotsprings/1851/paper.htm as at least Nov. 24, 1998.

Kenneth Clare, et al., Algin, Chapter 6, pp. 105–143 (1993).

* cited by examiner

*Primary Examiner*—Phyllis G. Spivack
(74) *Attorney, Agent, or Firm*—Piper Rudnick LLP; Steven B. Kelber

(57) ABSTRACT

A modified alginate and/or modified pectin composition for preventing and/or treating diseases and/or conditions caused by circulating agents such as poisonous heavy metals, environmental toxins, calcium and cholesterol, is provided. The composition includes a modified alginate having a molecular weight of no more than 40,000 daltons and/or a modified pectin having a molecular weight of no more than 40,000 daltons. The method involves orally or intravenously administering the modified alginate and/or modified pectin composition, alone or with excipients.

17 Claims, No Drawings

COMPOSITIONS AND METHODS FOR TREATING MAMMALS WITH MODIFIED ALGINATES AND MODIFIED PECTINS

This application is a Continuation-In-Part of application Ser. No. 09/255,265, filed Feb. 23, 1999 (allowed) now U.S. Pat. No. 6,274,566 the entirety of which is incorporated herein by reference.

BACKGROUND OF THE INVENTION

1. Field of the Invention

The present invention generally relates to low molecular weight alginate and/or pectin compositions and methods of using the same. The low molecular weight alginate and/or pectin compositions, which bind to various agents, including disease agents, heavy metals and other substances, protect mammals from and treat mammals with diseases and conditions. The low molecular weight alginate and/or pectin compositions are particularly useful in removal of deleterious agents or deleterious amounts of indigenous agents from a patient's blood supply and are therefore useful in heavy metal and environmental toxin removal as well as in calcium and cholesterol removal for treatment of arteriosclerosis.

2. Background of the Technology

It is well known that gelling agents may be effective in binding to a variety of substances, in vitro. While high molecular weight binding substances are known, due to their size, it is difficult for such substances to pass various blood barriers, including the gut or to circulate freely in the bloodstream. This is also, in part, because their solubility in water is generally too low.

Cancer metastasis is a stage of cancer which frequently marks conversion to an incurable disease. Most cancers share the ability to metastasize. In the metastatic process, cancer cells depart from the primary tumor, invade the basement membrane, traverse the bloodstream as tumor cell emboli and interact with the vascular endothelium of the target organ. There, the cancer cells proliferate to form secondary colonies. Kohn, Anti-Cancer Res., 13:2553–2259 (1993). It has been demonstrated that oral administration of modified citrus pectin, i.e., low molecular weight pectin, may be effective in suppressing or preventing metastases, by binding to residues on cancer cell surfaces, presumably through interaction between galactosyl residues o n the modified pectin with surface galectin-3, a carbohydrate binding protein on the surface of cancer cells. Pienta et al., J. Nat. Cancer Inst. 87, 348–353 (1995). It has also been demonstrated in application Ser. No. 09/255,265 that like modified pectin, modified alginate is effective in preventing and/or treating the metastatic process.

Cancer cells are not the only inimical elements circulating in mammalian blood. In many cases, diseases and/or conditions are mediated by circulating inorganic and/or organic agents. Thus, deleterious agents or even increased amounts of indigenous sub stances can induce such diseases or conditions. For example, calcium has been associated with a number of disease conditions, including arteriosclerosis and calcinosis. Arteriosclerosis is also influenced by the presence of cholesterol in the bloodstream.

While there are a variety of treatments for removal of detrimental amounts of circulating agents such as heavy metals, typically, these embrace removal, and treatment of portions of a patient's blood supply and reintroduction to the patient.

Algin and pectin, or alginates or pectinates digestion products of each, are known gelling agents. Algins and pectins occur naturally; a chief source of algins is seaweed; a chief source of pectins is citrus. Alginates are formed by a mixture of polymannuronic acid and polyguluronic acid. Repeating sub-units are bound by glycosidic links at the 1a-4a-di-axial position (polyguluronic acid) while repeating sub-units of polymannuronic acid are bound by galactic links at the 1e–4e di-equatorial position. Pectins are polymers of galacturonic acid that may be partially esterified. Naturally occurring algins and naturally occurring pectins are high molecular weight products. Both can, however, be reduced to low molecular weight products (defined herein as 40,000 daltons or less) by either chemical treatment (e.g., alkaline hydrolysis) or enzymatic degradation.

Alginates generally have superior protein recovery rates when compared to pectins of relatively similar molecular weight. Clare, Industrial Gums (1993 $3^{rd}$ Edition). Alginates therefore may exhibit a stronger binding ability than pectins for many substances.

Besides binding cancer cells, alginates are known to be effective metal binding compounds. This, along with the superior recovery rate associated with alginates, lends support that alginates would be useful in the prevention and/or treatment of diseases and/or conditions.

U.S. Pat. No. 5,141,927 discloses the use of an alginate and vitamin D composition to treat hypertension.

U.S. Pat. No. 5,597,810 discloses the use of an alginate-cholesterol compound to attract undesired lipids in the fluid media of the digestive tract prior to their absorption across cells lining the tract.

U.S. Pat. Nos. 5,283,086 and 5,324,526 disclose an algin-containing food or beverage as a source of dietary fiber. The patents disclose that the algin-containing food or beverage, which contains an aqueous solution of an algin having a weight average molecular weight in the range from about 10,000 to about 150,000, can be used to suppress the absorption of harmful substances in the digestive tract.

Japanese Patant No. 09235234 (Abstract) discloses the use of alginate oligosaccharides in the intestine to treat hyperlipidemia and arteriosclerosis.

Kimura et al., J. Ethnopharmacol, 54(1):47–54 (1996) (Abstract), discloses a study of natural sodium alginate (AG-270 (i.e., 2,700 kDa)) and three low-molecular weight sodium alginates (AG-1 (10 kDa), AG-5 (50 kDa) and AG-10 (100 kDa)) on cholesterol excretion and glucose tolerance in rats. Kimura et al. discloses that the study revealed that the natural sodium alginate and two of the three modified sodium alginates enhanced cholesterol secretion and inhibited blood glucose levels from rising after glucose administration. The authors noted that the results suggest that the effects of natural sodium alginate and AG-5 and AG-10 on cholesterol excretion and glucose tolerance may be due to inhibition of cholesterol and glucose adsorption from the small intestine by gelling of free alginic acid converted in the stomach and that these alginates can be used in the treatment/prevention of obesity, hypercholesterolemia and diabetes.

None of the references discussed above disclose substances that bind deleterious agents or deleterious amounts of indigenous agents in the bloodstream. In particular, none of the references discussed above disclose substances that are able to be absorbed through the intestinal mucosa, enter the bloodstream and exert their effects. In addition, none of the references discussed above disclose chelation and removal of heavy metals. Accordingly, there is a need to provide a composition and method by which disease and/or conditions caused by deleterious agents or deleterious amounts of indigenous agents circulating in the bloodstream can be prevented or reduced.

It is an object of the invention to provide a safe and effective treatment for high circulating amounts of detrimental agents such as heavy metals and environmental toxins.

It is an additional object of the invention to provide a safe and effective treatment for high circulating amounts of indigenous agents such as calcium and other minerals which contribute deposits such as calcinosis (large calcium deposits present in auto-immune condition like dermatomyositis) as well as cholesterol in order to prevent and or treat atherosclerosis. A further object is to provide a method for treating arteriosclerosis with reduced side effects.

SUMMARY OF THE INVENTION

The above objects, and other objects that are made clear by the discussion below, are met by the oral or the intravenous administration of modified alginates, modified pectins, or a combination of both, alone or together with promoter compounds.

For the prevention and/or treatment of diseases and/or conditions, modified alginates and/or modified pectins are employed herein. Modified alginates and modified pectins refer to low molecular weight products, i.e., no more than 40,000 daltons, obtained by hydrolysis or enzymatic digestion of algin or pectin.

Low molecular weight alginates and/or low molecular weight pectins can be used in chelation therapy, that is, administration to bind heavy metals, toxins and calcium in the bloodstream. While these potential poisons (including mercury, lead, arsenic, radioactive materials and others) can be chelated in the intestine, the inventive composition and method are particularly effective to chelate heavy metals circulating in the bloodstream. The chelation of calcium, as well as cholesterol binding, is effective in the treatment of arteriosclerosis.

Methods for modifying pectins to obtain low molecular weight pectins are known to those of skill in the art and can be obtained from commercial sources. See, e.g., Pienta, et al. Modified alginates are produced by a similar method, either through alkaline hydrolysis or enzymatic degradation using alginate lyase. The final modified alginate or pectin must be water soluble and have a weight average molecular weight of 40,000 daltons or below. Preferably, the modified alginate or modified pectin has a weight average molecular weight between about 10,000 daltons and about 20,000 daltons. More preferably, the modified alginate or modified pectin has a weight average molecular weight of about 10,000 daltons. Also, preferably, the modified alginate or modified pectin has a degree of esterification of less than about 10%. It may be combined with pharmaceutically acceptable carriers suitable for oral or intravenous administration, depending on the treatment method desired. Dosage levels will vary from 5–1500 mg per kg of body weight, per day, and may be sustained over a prolonged period. A preferred range may be 10 mg/kg/day to 1,000 mg/kg/day.

The invention itself together with further objects and advantages, will best be understood by reference to the following detailed description.

DETAILED DESCRIPTION OF THE INVENTION

For the treatment or prevention of diseases and/or conditions, modified alginates and/or modified pectins are used, either alone, or in combination. In other methods of treatment described herein, modified alginates or modified pectins, or their combination, may effectively be used.

A water soluble, low molecular weight modified alginate is prepared from alginic acid. An aqueous suspension is prepared, and the pH is adjusted to 10.0 with the addition of a hydroxide, suitably sodium hydroxide, for 30 minutes. This is followed by a reduction to a pH of 3.0 by the addition of HCl, according to the method of Albersheim, et al., Arch. Biochem. Biophys., 90:46–49 (1960). pH modification is conducted at temperatures of 85–95° C. for a period of up to 24–48 hours. After thermal degradation over an interval lasting 8–48 hours, sodium hydroxide and/or potassium hydroxide are added to equilibrate the modified alginate to a pH of approximately 6.0–6.5. The process may be monitored throughout the thermal degradation stage, to evaluate molecular weight. The essential characteristics of the inventive modified alginate is that it be water soluble and of a molecular weight below 40,000 daltons. This is necessary to ensure adequate passage of the modified alginate to the blood during digestion. The modified alginate may be dried by drum or spray drying.

In an alternate, more preferred process, the alginic acid is degraded enzymatically, rather than thermally. In this process, an aqueous preparation of alginic acid is modified to a pH of 3.0–6.0, with an optimum pH value of about 4.5, using a mixture of sodium and potassium hydroxide. The concentration of alginic acid in the aqueous preparation for both thermal and enzymatic degradation is approximately 10–30%. In the enzymatic degradation, the temperature for maximum enzymatic activity is 30–40° C., and is maintained over a period of 5–7 days. As the case with thermal degradation, the enzymatic degradation process can be monitored to evaluate the molecular weight. The enzymatic process, which permits attainment of more accurate molecular weight and esterification of final product, allows for better standardization, better quality control and reproducible results. (Molecular weight herein is weight average molecular weight). pH is adjusted to a value of 6.0–6.5, and the solution is dried by drum or spray drying.

A principle method of using the modified alginate of the invention is in the prevention or treatment of diseases and/or conditions caused by deleterious circulating agents. Because the individual units of modified alginates, guluronic acid and mannuronic acid, can be linked and cross-linked in a variety of different fashions (and obtained that way from a variety of different seaweeds) the resulting units can be presented in a variety of concentrations and accessibilities. Preferably, a large variety of modified alginate is employed to maximize the likelihood that effective binding between the modified alginate and deleterious circulating agents in the bloodstream can be achieved. It is believed that certain modified alginate configurations, including reduced cross-linking, and a high degree of alternating monomers may result in the exposure of greater binding units, providing for greater effectiveness.

In accordance with an embodiment of the invention, modified alginate and/or modified pectin is administered to chelate poisonous metals, including mercury, lead, nickel and others, that may be circulating in the blood. Blood poisoning due to the presence of heavy metals and related toxins can be treated by administration of modified alginate and/or modified pectin to bind the discreet metal particles. In this respect, modified alginate and modified pectin are gelling agents, and the bound particles/gel are safely removed by the body. Dosage levels for this type of treatment can be on the order of 50–1,000 mg of modified alginate and/or modified pectin per kg body weight. It should be noted that many poisonous metals enter the bloodstream through accidental or unintentional ingestion, pollution and ingestion of amalgam from silver fillings and other metals during dental work and from leakage. The modified alginate or modified pectin of the invention is of sufficient molecular weight and is water-soluble to be readily absorbed through the intestinal mucosa into the bloodstream. Oral administration of modified alginate and/or modified pectin in this method effectively isolates and removes dangerous metals whether present intestinally or in the bloodstream. Metals such as aluminum, antimony, beryllium, bismuth, mercury, platinum, thallium, thorium, tin, tungsten, uranium, lead, mercury, cadmium, arsenic, silver, nickel, radioactive metals and mixtures thereof, which (1) are frequently concentrated by plants and animals that constitute part of the food chain or (2) are otherwise present in the environment and (3) are recognized toxins that may effectively be removed by this method. In addition, additional toxins such as MTBA and dioxin may also be removed.

The present invention will be further illustrated by the following non-limiting Example

EXAMPLE

The modified alginate and/or modified pectin may be employed to bind heavy metals in the blood stream as follows:

Patients that are known to have increased levels of toxic metals (e.g., lead, mercury, cadmium, etc.) as determined through physical exams, specific questionnaires and hair analysis are chosen. Patients having heavy metal toxicity are entered into the study.

Modified alginate and/or modified pectin with or without excipient is administered to bind heavy metals in the blood stream and facilitate heavy metal excretion via the urinary tract. For example, modified alginate and/or modified pectin powder encapsulated into gelatin capsules in the amount of 800 mg/capsule may be employed. Alternatively, a water-based preparation could be used. Dosage may be 6 capsules taken three times a day with 8 full ounces of water or juice.

An open labeled, non-controlled study with prescreened patients known to have heavy metal burdens that exceed the normal range is conducted. Ten pre-screened patients (ages 18–75) are monitored under semi-controlled conditions using questionnaires, and are evaluated for heavy metal toxicity at baseline, and again at one week and three week time points in the study. All samples are taken under the control of a qualified medical professional.

Heavy metal burden is measured at time zero and at one and three weeks respectively to determine if the oral administration of modified alginate and/or modified pectin (<40,000 daltons) (1) is absorbed into the blood stream, (2) is bound with heavy metals and (3) is able to facilitate heavy metal excretion into the urine.

The modified alginate and/or modified pectin may be administered orally or intravenously. Alginates and pectins have been shown to be well tolerated through both methods of administration. A daily dosage of about 15 grams of modified alginate is believed to be effective, but dosages can vary from 5 mg of modified alginate per kg of body weight on up to 1,000–1,500 mg of modified alginate per kg of body weight, and more, per day.

Protocol

1) Pre-qualified patients will be measured for heavy metal toxicity burden using standard urine analysis by a qualified FDA approved laboratory.

2) Analysis will establish the baseline levels and mid and end-point levels for a variety of heavy metals including but not limited to $Pb^{+2}$, $Hg^{+2}$, $Cd^{+2}$ and As.

3) Patients will be enrolled in an opened labeled, non-controlled trial and supplemented with a novel form of modified alginate and/or modified pectin (<40,000 daltons). Dosages will be based on 800 mg capsules to be taken as six (6) capsules three times a day (total=14.4 grams) of the modified alginate and/or modified pectin product.

4) All patients will receive a three week's supply of alginate and/or modified pectin capsules at a time and compliance will be measured by a questionnaire and the honor system.

5) A qualified professional will collect urine samples at time 0 (baseline) and again at one week and three-week time points. The study will be concluded after three weeks and all data will be collected and analyzed.

Evaluations

1) All data will be collected at the start of the study and at one week and the endpoint at 3 weeks (21 days).

2) A FDA certified medical laboratory would process all urine samples using ICP-MS technology.

3) Results on toxic metal levels in the urine will be reported as mcg/g creatine and as mcg/24 hour urine. These will account for urine dilution variations that may occur and are a standard measure of toxic burden and monitoring of toxic detoxification.

4) Analytical results will be compiled and compared against baseline values using appropriate statistical methods.

Patients that show a statistically significant change in various toxic elements will be indicative of the absorption and binding of heavy metals via the bloodstream. Increased levels of heavy metals as reflected in urine samples will demonstrate the ability of modified alginates to specifically:

1) Be absorbed into the blood stream following oral ingestion.
2) Bind with various heavy metals circulating in the bloodstream, and
3) Facilitate the removal of heavy metals via the urinary tract.

The protocol discussed above can also be used to determine the effects of the modified alginate and/or modified pectin (and any excipient) on additional deleterious circulating agents, e.g., environmental toxins, and deleterious amounts of indigenous agents.

The modified alginate and/or modified pectin may be administered alone, or together with agents which enhance binding, such as whey protein (rich in glutathione), selenium and related binding adjuvants. Additional effective agents are those which aid excretion through both the kidneys and intestines, such as diuretics, phase two initiators such as sulfired amino acids, EDTA, etc.

Neither modified alginate nor modified pectin is known to have any side effects, or to exhibit cytopathology or toxicology. Oral administration can be a reconstitution of dried modified alginate and/or modified pectin in water or other suitable solution, or using a wide variety of conventional excipients, vehicles, flavorings and the like. Additional ingredients such as phase II detoxification enhancers, botanicals, anti-oxidants, sulfured amino acids, EDTA, curcumin, indoles such as 13C, selenium, zinc and glutathione, may be used to potentiate the effects of the modified alginate and/or modified pectin composition. Higher molecular weight align and/or pectin may also be added to the modified alginate or modified pectin composition to enhance binding of substances in the intestine. Controlled dosage formulations are preferred to ensure adequate medication over time.

In this respect, the administration of modified alginate may be doubly effective in the treatment of diseases characterized by an inadequate immune response. As noted previously, the modified alginate of the invention is comprised of guluronic and mannuronic acid monomers. Unbound mannuronic acid is broken down by the body to uronic acid and mannose. It is known that the administration of mannose stimulates the immune system. Turner, Scand. J. Immunol., 48(2):124–126 (1998); Kakkanaiah et al., Clin. Diagn. Lab Immunol., 5(3):319–321 (1998). To achieve significant immune stimulation, modified alginate levels should be on the order of 10–15 grams/day.

The present inventors have also observed that the inventive modified alginate and/or modified pectin is capable of binding circulating calcium and circulating cholesterol. Effective binding of circulating calcium (although not all calcium) and circulating cholesterol are effective methods for preventing and/or treating arteriosclerosis. The invention permits binding of calcium and cholesterol beyond the intestines. By binding these circulating indigenous agents, deposit of plaque on the endothelial walls is prevented, thus providing an effective method of treating arteriosclerosis and related conditions, including hypertension and coronary heart disease, without significant side effects. In the prevention and/or treatment of target individuals who may be at risk of developing severe arteriosclerosis, dosage values of 2–15 grams of modified alginate and/or modified pectin per day, or in the range of 150 mg of modified alginate and/or modified pectin per kg body weight, is appropriate.

The invention has been described by both specific example, and generic description. Alternatives, particularly alternatives with respect to the composition and characteristics of modified alginate and/or modified pectin, as well as treatment regimen, will occur to those of ordinary skill in the art, without the exercise of inventive faculty. Such alternatives remain within the scope of the invention, unless specifically excluded by the recitation of the claims set forth below.

What is claimed is:

1. A method of treating or preventing poisoning in a mammal which is caused by circulation in the blood of said mammal of a poison selected from the group consisting of toxic metals, enviromental toxins and mixtures thereof, comprising administering to a marnmal in need of same an effective amount of modified alginate having a molecular weight of no more than 40,000 daltons, and obtained by hydrolysis or enzymatic degradation of alginic acid, in an amount to effectively bind said poison.

2. The method of claim 1, wherein said poisoning is metal poisoning, and said poison is a poisonous heavy metal.

3. The method of claim 2, wherein said heavy metal is selected from the group consisting of aluminum, antimony, beryllium, bismuth, mercury, platinum, thallium, thorium, tin, tungsten, uranium, lead, mercury, cadmium, arsenic, silver, nickel, radioactive metals and mixtures thereof.

4. The method of claim 3, wherein administration of said modified alginate is accompanied by administration of modified pectin having a molecular weight of no more than 40,000 daltons obtained by hydrolysis or enzymatic degradation of pectin.

5. The method of claim 1, wherein said modified alginate is administered orally or intravenously.

6. The method of claim 5, wherein said modified alginate is administered orally in an amount of from 5–1,500 mg per kg body weight per day.

7. The method of claim 5, wherein said modified alginate is administered intravenously in an amount of from 1–1,000 mg per kg body weight per day.

8. A method of treating or preventing poisoning in a mammal which is caused by circulation in the blood of said mammal of a poison selected from the group consisting of toxic metals, environmental toxins and mixtures thereof, comprising administering to a mammal in need of same an effective amount of modified pectin having a molecular weight of no more than 40,000 daltons, and obtained by hydrolysis or enzymatic degradation of pectin, in an amount to effectively bind said poison.

9. The method of claim 8, wherein said poisoning is metal poisoning, and said poison is a poisonous heavy metal.

10. The method of claim 9, wherein said heavy metal is selected from the group consisting of aluminum, antimony, beryllium, bismuth, mercury, platinum, thallium, thorium, tin, tungsten, uranium, lead, mercury, cadmium, arsenic, silver, nickel, radioactive metals and mixtures thereof.

11. The method of claim 8, wherein said modified pectin is administered orally or intravenously.

12. The method of claim 11, wherein said modified pectin is administered orally in an amount of from 5–1,500 mg per kg body weight per day.

13. The method of claim 11, wherein said modified pectin is administered intravenously in an amount of from 1–1,000 mg per kg body weight per day.

14. A method of treating or preventing arteriosclerosis caused by circulation of calcium in the blood of a mammal, comprising administering to said mammal modified alginate having a molecular weight of no more than 40,000 daltons, and obtained by hydrolysis or enzymatic degradation of alginic acid, in an amount to effectively bind said calcium.

15. The method of claim 14, wherein said amount is 2–15 grams of modified alginate per day.

16. A method of treating or preventing arteriosclerosis caused by circulation of calcium in the blood of a mammal, comprising administering to said mammal modified pectin having a molecular weight of no more than 40,000 daltons, and obtained by hydrolysis or enzymatic degradation of pectin, in an amount to effectively bind said calcium.

17. The method of claim 16, wherein said amount is 2–15 grams of modified pectin per day.

* * * * *